(12) United States Patent
Walter

(10) Patent No.: US 9,033,184 B2
(45) Date of Patent: May 19, 2015

(54) BLADE DISPENSER

(71) Applicant: Leica Biosystems Nussloch GmbH, Nussloch (DE)

(72) Inventor: Roland Walter, Reilingen (DE)

(73) Assignee: LEICA BIOSYSTEMS NUSSLOCH GMBH, Nussloch (DE)

( * ) Notice: Subject to any disclaimer, the term of this patent is extended or adjusted under 35 U.S.C. 154(b) by 29 days.

(21) Appl. No.: 13/948,254

(22) Filed: Jul. 23, 2013

(65) Prior Publication Data

US 2014/0034665 A1 Feb. 6, 2014

(30) Foreign Application Priority Data

Aug. 3, 2012 (DE) .................. 10 2012 213 810

(51) Int. Cl.
*G07F 11/00* (2006.01)
*A47F 1/00* (2006.01)
*B65D 83/08* (2006.01)
*B65D 83/10* (2006.01)

(52) U.S. Cl.
CPC .............. *B65D 83/08* (2013.01); *B65D 83/10* (2013.01)

(58) Field of Classification Search
CPC ............... B65D 83/10; B65D 83/0888; B65D 83/0409; B65D 83/02; B65D 2209/00; A47K 10/45; G07F 11/04; G07F 11/44
USPC .................. 221/257, 256, 255, 102, 268, 232
See application file for complete search history.

(56) References Cited

U.S. PATENT DOCUMENTS

| | | | | |
|---|---|---|---|---|
| 1,490,070 | A | * | 4/1924 | Korth .............................. 221/47 |
| 2,182,615 | A | * | 12/1939 | Johnson ......................... 206/359 |
| 2,685,364 | A | * | 8/1954 | Treiss ............................ 206/360 |
| 2,822,916 | A | * | 2/1958 | Wark et al. ..................... 206/228 |
| 3,070,260 | A | * | 12/1962 | Smith ............................ 221/102 |
| 3,080,998 | A | * | 3/1963 | La Cas ........................... 221/232 |
| 3,089,583 | A | * | 5/1963 | White ............................ 206/233 |
| 3,151,738 | A | * | 10/1964 | Stone ............................. 206/204 |
| 3,193,139 | A | * | 7/1965 | Iannone et al. ................ 221/224 |
| 3,270,915 | A | * | 9/1966 | Auer .................................. 221/2 |
| 3,459,329 | A | * | 8/1969 | Mochizuki et al. ............. 221/34 |
| 3,460,712 | A | * | 8/1969 | Lowry ........................... 221/102 |
| 3,542,245 | A | * | 11/1970 | Braginetz ...................... 221/232 |
| 3,543,918 | A | * | 12/1970 | Borden et al. ................. 206/356 |

(Continued)

FOREIGN PATENT DOCUMENTS

| | | | | |
|---|---|---|---|---|
| DE | 3538768 A1 | * | 5/1987 | ............. B65D 83/10 |
| GB | 2445079 A | | 6/2008 | |

(Continued)

*Primary Examiner* — Rakesh Kumar
(74) *Attorney, Agent, or Firm* — Hodgson Russ LLP

(57) ABSTRACT

A blade dispenser (100) has a blade supply container (110), a blade disposal container (120), and a detachable and reconnectable connecting means (130, 131, 132) that is embodied to connect the blade supply container (110) and blade disposal container (120) detachably to one another. The blade supply container (110) has a blade supply container upper side and a blade supply container underside, and is embodied to receive a blade stack (111) made up of multiple mutually abutting blades (112, 115). The blade supply container (110) also has a removal opening (116) through which at least one blade (112, 115) of the blade stack (111) is removable from the blade supply container (110). The blade disposal container (120) has a blade disposal container upper side and a blade disposal container underside, and is embodied to receive blades (120) to be disposed of.

25 Claims, 2 Drawing Sheets

(56) References Cited

U.S. PATENT DOCUMENTS

Figure 1:
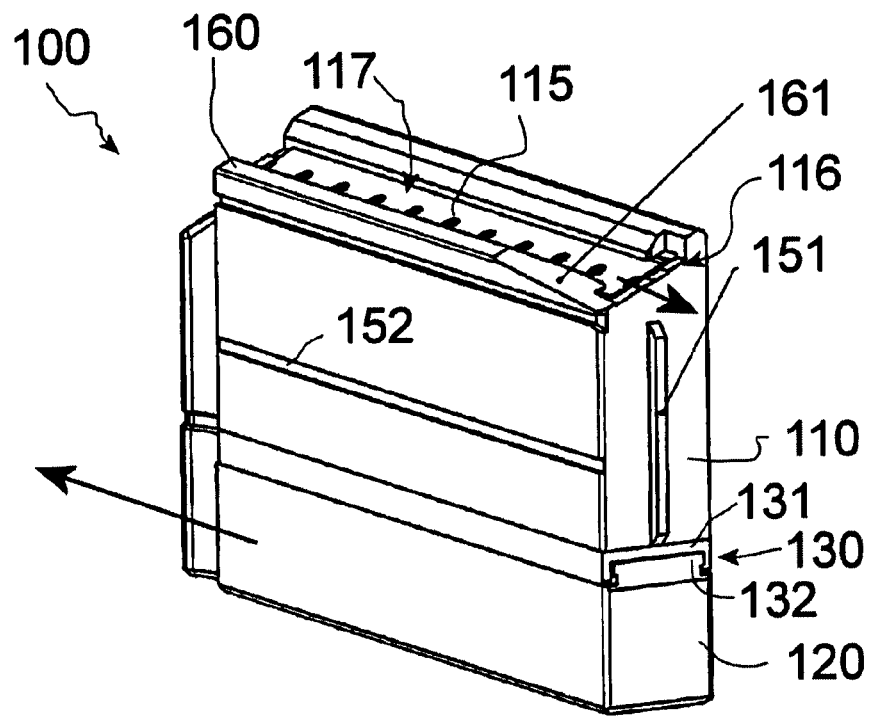

| | | | | |
|---|---|---|---|---|
| 3,549,046 | A * | 12/1970 | Iten | 221/102 |
| 3,588,988 | A * | 6/1971 | Maguire | 9/429 |
| 3,650,433 | A * | 3/1972 | Robertson | 221/65 |
| 3,783,493 | A * | 1/1974 | Dawidowicz et al. | 221/1 |
| 3,833,146 | A * | 9/1974 | Braginetz | 221/66 |
| 3,848,770 | A * | 11/1974 | Iten | 221/102 |
| 3,850,343 | A * | 11/1974 | Petrillo | 221/102 |
| 3,880,321 | A * | 4/1975 | Braginetz | 221/66 |
| 3,910,455 | A * | 10/1975 | Ferraro | 221/102 |
| 4,045,102 | A * | 8/1977 | Austin | 312/61 |
| 4,073,407 | A * | 2/1978 | Pentney | 221/102 |
| RE29,571 | E * | 3/1978 | Dawidowicz et al. | 30/40.2 |
| 4,106,620 | A | 8/1978 | Brimmer et al. | |
| 4,182,033 | A * | 1/1980 | Jacobson et al. | 30/169 |
| 4,207,790 | A * | 6/1980 | Endo | 83/699.11 |
| 4,379,514 | A * | 4/1983 | Joffe | 221/279 |
| 4,471,885 | A * | 9/1984 | Mucciarone | 221/155 |
| 4,524,884 | A * | 6/1985 | Myers | 221/231 |
| 4,789,080 | A * | 12/1988 | Iten | 221/279 |
| 4,850,512 | A * | 7/1989 | Vujovich | 221/232 |
| 4,946,031 | A * | 8/1990 | Confalonieri | 206/38 |
| 5,123,551 | A * | 6/1992 | King | 221/34 |
| 5,251,783 | A * | 10/1993 | Gringer | 221/102 |
| 5,388,693 | A * | 2/1995 | Ceraudo | 206/340 |
| 5,456,382 | A * | 10/1995 | Gringer | 221/257 |
| 5,927,488 | A * | 7/1999 | Gray | 206/237 |
| 5,937,522 | A * | 8/1999 | Althaus et al. | 30/40.2 |
| 6,000,871 | A * | 12/1999 | Fisher, Sr. | 400/706 |
| 6,158,616 | A * | 12/2000 | Huang | 221/268 |
| 6,472,220 | B1 * | 10/2002 | Simons et al. | 436/63 |
| 6,508,380 | B1 * | 1/2003 | von Schuckmann | 221/4 |
| 6,598,761 | B1 * | 7/2003 | Chou | 221/228 |
| 6,796,455 | B2 * | 9/2004 | Schmidt | 221/256 |
| 6,892,898 | B1 * | 5/2005 | Boone et al. | 221/36 |
| 7,059,493 | B2 * | 6/2006 | Welchel et al. | 221/34 |
| 7,118,008 | B2 * | 10/2006 | Hsu | 221/45 |
| 7,146,894 | B2 * | 12/2006 | Hendrick et al. | 83/703 |
| 2002/0162847 | A1 * | 11/2002 | Roy | 221/34 |
| 2003/0015545 | A1 | 1/2003 | Graupner | |
| 2003/0085236 | A1 * | 5/2003 | Schmidt | 221/232 |
| 2004/0168995 | A1 * | 9/2004 | Ignoffo et al. | 211/51 |
| 2006/0272467 | A1 * | 12/2006 | Hendrick et al. | 83/730 |
| 2008/0148918 | A1 | 6/2008 | Thiem et al. | |
| 2009/0235799 | A1 | 9/2009 | Thiem | |
| 2009/0236357 | A1 * | 9/2009 | Giraud et al. | 220/849 |
| 2011/0139648 | A1 * | 6/2011 | Sonnenberg | 206/354 |
| 2011/0139649 | A1 * | 6/2011 | Marcinkowski | 206/354 |
| 2011/0233229 | A1 * | 9/2011 | Schekalla | 221/270 |
| 2012/0097678 | A1 * | 4/2012 | Giraud et al. | 220/260 |
| 2014/0033888 | A1 * | 2/2014 | Walter | 83/698.11 |
| 2014/0034665 | A1 * | 2/2014 | Walter | 221/102 |

FOREIGN PATENT DOCUMENTS

| | | |
|---|---|---|
| JP | 2000-62869 A | 2/2000 |
| WO | 01/84110 A2 | 8/2001 |

* cited by examiner

BLADE DISPENSER

CROSS REFERENCE TO RELATED APPLICATIONS

This application claims priority of German patent application number 10 2012 213 810.2 filed Aug. 3, 2012, the entire disclosure of which is incorporated by reference herein.

FIELD OF THE INVENTION

The present invention relates to a blade dispenser for microtome blades.

BACKGROUND OF THE INVENTION

Microtomes are used, for example, to prepare thin sections of tissue that can then be investigated microscopically. Microtomes have for this purpose a knife holder having a very sharp blade. Disposable blades have become established in particular in the laboratory sector, a blade being disposed of after a number of sectioning operations and replaced with a new blade. One such knife holder is described in DE 10 2004 051 974 A1. Here the blades must be changed manually. As an improvement, DE 10 2007 006 826 B1 describes a knife holder in which blade changing is assisted by a driver. New blades are taken out of a blade supply container in which a blade stack made up of multiple blades is received in spring-loaded fashion. Blades to be disposed of are disposed of into a blade disposal container. DE 28 52 373 C2 discloses a blade dispenser having an integrated blade disposal container, although the blades must be conveyed into it manually.

It is desirable to improve the handling of the blade disposal container in particular for the case in which an automatic or mechanically assisted disposal of used blades is desired, in particular in blade changing apparatuses.

SUMMARY AND ADVANTAGES OF THE INVENTION

The present invention proposes a blade dispenser having a blade supply container, a blade disposal container, and a detachable and reconnectable connecting means for connecting the blade supply container and blade disposal container detachably to one another. The blade supply container includes a blade supply container upper side and a blade supply container underside, and is embodied to receive a blade stack made up of multiple mutually abutting blades. The blade supply container further includes a removal opening through which at least one blade of the blade stack is removable from the blade supply container. The blade disposal container includes a blade disposal container upper side and a blade disposal container underside, and is embodied to receive blades to be disposed of.

A blade dispenser according to the present invention is particularly well suited for use in mechanically assisted or fully automatic blade changing apparatuses. The blade supply container and blade disposal container of the blade dispenser can be separated from one another, and thus arranged at associated positions in the blade changing apparatus. After use, for example when all the blades are used or when a different type of blade from a different blade dispenser is to be used, they can be connected to one another again so that no container or blade can become lost. Once all the blades are used, the entire blade dispenser can be disposed of.

A blade stack made up of multiple blades that serve for use in a microtome is received in a full blade supply container. The blade stack is preferably spring-loaded, so that it is pressed against an upper side of the blade supply container. For purposes of the invention and without restriction, that side of a blade supply container against which the blade stack is pressed, and at which a removal of the blades takes place, is referred to as the "upper side." The uppermost blade of the stack is therefore the one that is in a removal position. In corresponding fashion, for purposes of the invention and without restriction, that side of a blade disposal container at which the blade to be disposed of is introduced is referred to as the "upper side."

The main extension plane or body plane of at least the next blade to be removed, or of several or of all blades, of the blade stack preferably extends not perpendicularly, but instead at an angle that is preferably less than 85° or less than 80°, to the stack direction. In most microtome knife holders, the blade extends in the installed state substantially vertically or slightly tilted with respect to the vertical. In order to facilitate the transfer of a blade out of the blade supply container into the knife holder, the orientation of the next blade to be removed from the blade supply container should already correspond substantially to the later orientation in the knife holder. An oblique placement in the blade supply container thus allows the horizontal installation space required for the blade supply container on the knife holder to be made smaller, since with a blade that extends approximately vertically, the blade supply container need not protrude horizontally. In order to achieve the obliquity, the blade stack can, for example, be supported on an (in particular, spring-loaded) support block having a correspondingly shaped cross section.

In an advantageous embodiment, the blade supply container comprises a bar on its upper side. The bar extends parallel to a direction in which blades are removed from the blade supply container. The bar can serve, for example, as a guide for blades to be disposed of, if provision is made that they are conveyed back toward the blade supply container for disposal. The bar can be beveled for this purpose at a removal-side end, thus making it easier for a blade to slide onto the bar while being conveyed back. The bevel can also influence the direction of the blade that is sliding on, in particular so it can be more effectively delivered to the blade disposal container.

The blade supply container preferably comprises a full indicator or an empty indicator that indicates, in particular, an empty blade supply container. An empty indicator can, for example, be blocked as long as blades are present in the blade supply container. The empty indicator is preferably embodied in such a way that it is actuated by a spring means that impinges upon the blade stack with spring force as soon as the last blade is removed. Preferably there is arranged, on that side of the blade stack which faces away from the spring means (this is also referred to in the context of the invention as "above" the blade stack), an element of the empty indicator which is to be impinged upon with spring force for actuation, e.g. a pin to be driven upward out of the blade supply container, actuation being prevented when blades are received in the blade supply container.

The blade supply container and/or blade disposal container usefully comprise alignment means that are embodied to enable exact arrangement and orientation of the respective container on a blade changing apparatus. The alignment means can comprise, for example, one or more flanges, grooves, or lugs that enable insertion of the container into a corresponding holder of the blade changing apparatus.

The blade supply container and/or blade disposal container usefully comprise a handling means that is embodied to permit simple handling by a user. The handling means can be embodied, for example, as a handle shaped onto the container.

Further advantages and embodiments of the invention are evident from the description and from the appended drawings.

It is understood that the features recited above and those yet to be explained below are usable not only in the respective combination indicated, but also in other combinations or in isolation, without departing from the scope of the present invention.

The invention is schematically depicted in the drawings on the basis of an exemplifying embodiment, and will be described in detail below with reference to the drawings.

BRIEF DESCRIPTION OF THE DRAWING VIEWS

Figure 2:
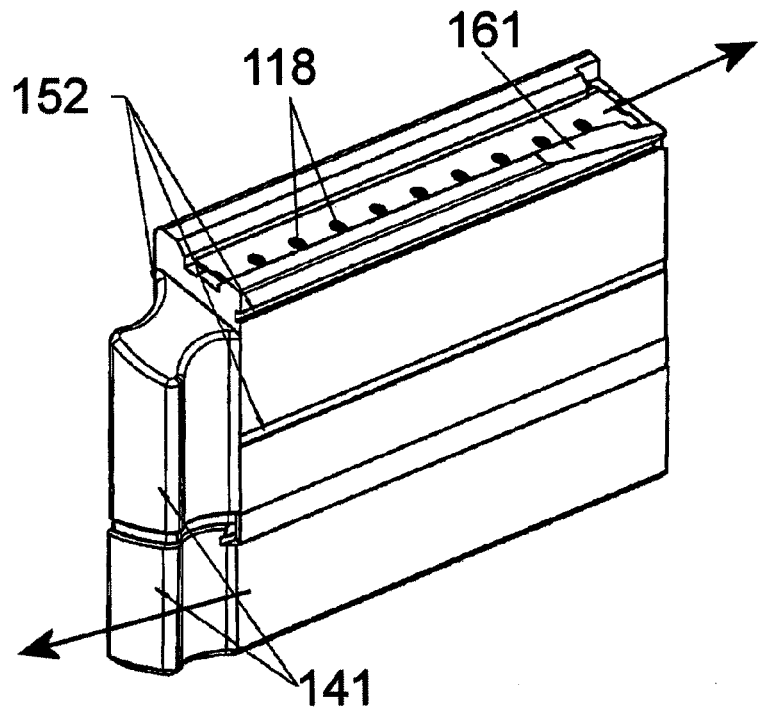
Figure 3:
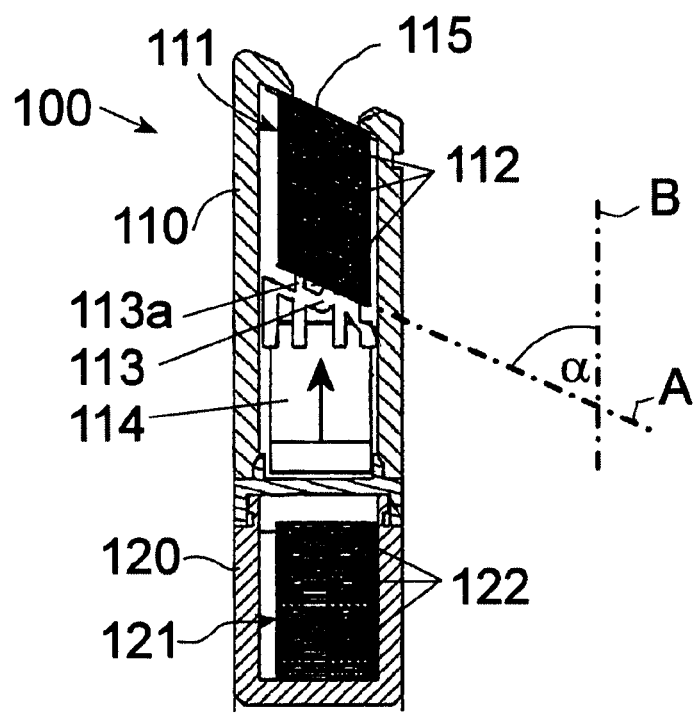
Figure 4:
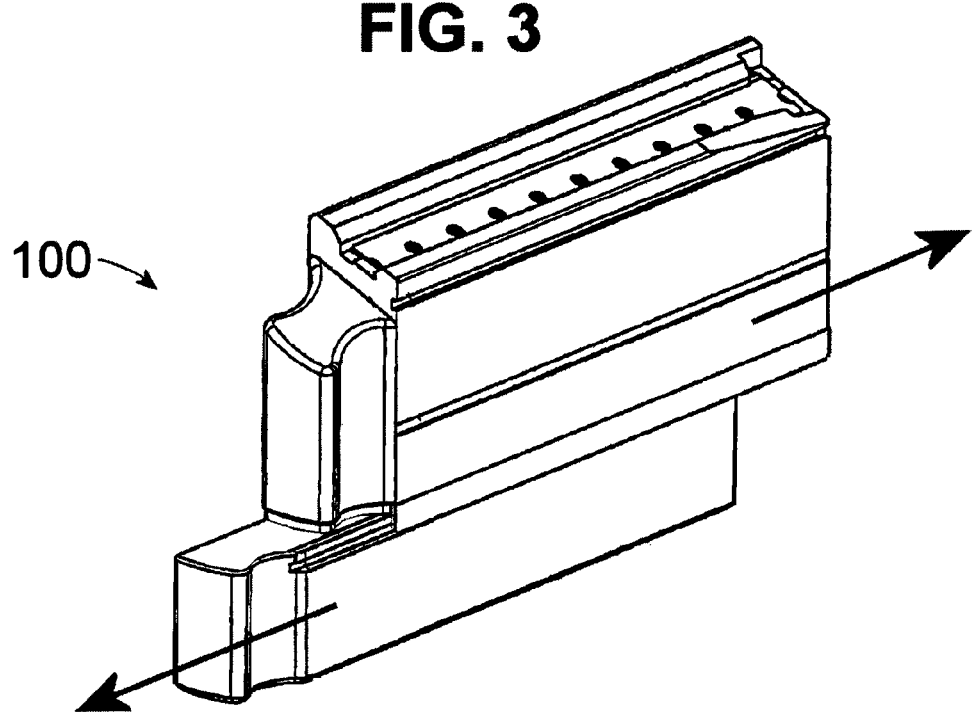

FIG. 1 is a perspective view of a preferred embodiment of a blade dispenser according to the present invention, FIG. 2 is another perspective view of the blade dispenser according to FIG. 1, FIG. 3 is a cross-sectional view of the blade dispenser of FIG. 1, and FIG. 4 shows the separability of the blade supply container and blade disposal container of the blade dispenser according to FIG. 2.

DETAILED DESCRIPTION OF THE INVENTION

FIGS. 1 to 4 are described below together and continuously, identical elements being labeled with identical reference characters. FIGS. 1 and 2 are perspective views of a preferred embodiment of a blade dispenser 100 according to the present invention.

Blade dispenser 100 comprises a blade supply container 110 as well as a blade disposal container 120 detachably and reconnectably connected thereto. As is evident, for example, in the sectional view of FIG. 3, a blade stack 111 made up of a plurality of blades 112, 115 is received in blade supply container 110, the uppermost blade being labeled 115. Blade stack 111 is supported on a support block 113 that is impinged upon with spring force by a spring means embodied as leaf spring 114. The spring force presses the support block upward so that uppermost blade 115 of the blade stack comes to rest in a removal position next to a removal opening 116.

The next blade to be removed is in this case always the uppermost one of blade stack 111. It can be slid out of the removal position and out of blade supply container 110 through removal opening 116, to the side, i.e. forward and to the right and forward and to the rear in FIGS. 1 and 2 respectively, and removed. Each blade 112, 115 of blade stack 111 comprises one or more engagement openings 118 into which a driver, in particular of a blade changing apparatus, can engage in order to move the blade, in particular in this case to push it out of removal opening 116 of the blade supply container. In order to enable access to blade 115 in the removal position, an access opening embodied as a slot 117 is provided in the upper side of blade supply container 110.

Blade disposal container 120 is embodied here as a container open on its upper side. Blade disposal container 120 is embodied to receive used blades 122, which are likewise received as a stack 121 in blade disposal container 120. Blades to be disposed of are introduced for that purpose into blade disposal container 120 on the upper side.

Blade dispenser 100 comprises a detachable and reconnectable connecting means 130 that detachably connects blade supply container 110 and blade disposal container 120 to one another. Connecting means 130 is embodied here as a slide closure in the manner of a dovetail guide, such that, as illustrated in FIG. 4, the connection can be released and created by sliding containers 110 and 120 with respect to one another. In the embodiment depicted, dovetail guide 130 comprises interengaging flanges 131 on the underside of the blade supply container and 132 on the upper side of the blade disposal container. As a consequence, the result of connecting the blade supply container and the blade disposal container is also that the upper side of blade disposal container 120 becomes closed off.

Once blade disposal container 120 has been fastened on blade supply container 110 by means of dovetail guide 130, the used blades are securely received and can easily be disposed of together with the empty blade supply container.

Handling means embodied as handles 141, which can be grasped by a user, are furthermore shaped onto blade supply container 110 and onto blade disposal container 120. Blade supply container 110 furthermore comprises multiple alignment means that are embodied as lug 151 and grooves 152 and serve to enable exact orientation (and preferably secure fastening) of blade supply container 110 on a blade changing apparatus. In an advantageous embodiment, blade disposal container 120 can also comprise alignment means.

Blade supply container 110 furthermore comprises a bar 160 having a beveled end 161, which bar can serve as a guide for used blades, for example when blade supply container 110 is incorporated into a blade changing apparatus. Beveled end 161 forms an inclined plane with respect to the blade supply container surface.

As is evident in particular in the cross-sectional view in FIG. 3, the bodies or main extension planes A of blades 115, 112 of blade stack 111 are arranged with respect to stack direction B at an angle $\alpha$ not equal to 90°. The angle $\alpha$ between A and B is in this case approximately 70°. This enables a space-saving arrangement of blade supply container 110 in a blade changing apparatus. For this purpose, support block 113 is embodied in cross section with a corresponding angle $\alpha$ between its upper side, on which the blade stack is supported, and the vertical axis of the blade supply container. Support block 113 is impinged upon from below with spring force by leaf spring 114.

According to the preferred embodiment depicted here, support block 113 is furthermore equipped with an empty indicator 113a that is embodied here as a (for example, colored) pin. Once the last blade of stack 111 has been removed, support block 113 is pressed against the upper side of blade supply container 110 so that pin 113a projects out of blade supply container 110 and can be detected as an empty indicator.

What is claimed is:

1. A blade dispenser (100) comprising:
 a blade supply container (110) including a blade supply container upper side and a blade supply container underside, the blade supply container (110) being embodied to receive a blade stack (111) made up of multiple mutually abutting blades (112, 115), the blade supply container (110) further including a removal opening (116) through which at least one blade (112, 115) of the blade stack (111) is removable from the blade supply container (110), the blade supply container (110) comprising an empty indicator (113a) embodied to indicate when no blade (112, 115) is received in the blade supply container (110), the blade supply container (110) comprising a spring means (114) arranged so that a blade stack (111) received in the blade supply container (110) is impinged upon with spring force, and the empty indicator (113a) is actuated by the spring means (114) when no blade (112, 115) is received in the blade supply container (110);

a blade disposal container (120) including a blade disposal container upper side and a blade disposal container underside, the blade disposal container (120) being embodied to receive blades (120) to be disposed of; and a detachable and reconnectable means for connecting (130, 131, 132) the blade supply container (110) and blade disposal container (120) detachably to one another.

2. The blade dispenser according to claim 1, wherein the detachable and reconnectable means for connecting (130, 131, 132) connects the blade supply container underside and the blade disposal container upper side detachably to one another.

3. The blade dispenser according to claim 1, an uppermost blade (115) of the blade stack (111) having a main extension plane (A), and the multiple mutually abutting blades (112, 115) being stacked in a stack direction (B) that encloses with the main extension plane (A) of the uppermost blade (115) an angle not equal to 90°.

4. The blade dispenser according to claim 3, the blade stack (111) being supported on a support block (113) which makes available a support surface that encloses with the stack direction (B) an angle not equal to 90°.

5. The blade dispenser according to claim 1, wherein the detachable and reconnectable means for connecting (130, 131, 132) includes a sliding closure.

6. The blade dispenser according to claim 5, wherein the sliding closure is configured as a dovetail guide.

7. The blade dispenser according to claim 1, wherein the detachable and reconnectable means for connecting (130, 131, 132) includes a snap-in closure.

8. The blade dispenser according to claim 1, wherein the detachable and reconnectable means for connecting (130, 131, 132) comprises, on the blade supply container (110) and on the blade disposal container (120), flanges (131, 132) that can be slid into one another.

9. The blade dispenser according claim 1, the blade supply container (110) further including an access opening (117) through which at least one blade (112, 115) of the blade stack (111) is accessible from outside the blade supply container (110).

10. The blade dispenser according to claim 9, the access opening (117) being embodied as an elongated hole on the blade supply container upper side.

11. The blade dispenser according to claim 1, the blade supply container (110) having a bar (160) on the blade supply container upper side (110), wherein the bar (160) forms an inclined plane (161) on the blade supply container upper side.

12. The blade dispenser (100) according to claim 4, wherein the empty indicator (113a) is arranged on the support block (113).

13. The blade dispenser (100) according to claim 1, wherein the blade supply container (110) comprises means for alignment (151, 152) embodied to orient the blade supply container (110) on a blade changing apparatus.

14. The blade dispenser (100) according to claim 1, wherein the blade disposal container (120) comprises means for alignment (151, 152) embodied to orient the blade disposal container (120) on a blade changing apparatus.

15. A blade dispenser (100) comprising:

a blade supply container (110) including a blade supply container upper side and a blade supply container underside, the blade supply container (110) being embodied to receive a blade stack (111) made up of multiple mutually abutting blades (112, 115), the blade supply container (110) further including a removal opening (116) through which at least one blade (112, 115) of the blade stack (111) is removable from the blade supply container (110), an uppermost blade (115) of the blade stack (111) having a main extension plane (A), and the multiple mutually abutting blades (112, 115) being stacked in a stack direction (B) that encloses with the main extension plane (A) of the uppermost blade (115) an angle not equal to 90°, the blade stack (111) being supported on a support block (113) which makes available a support surface that encloses with the stack direction (B) an angle not equal to 90°, the blade supply container (110) comprising an empty indicator (113a) embodied to indicate when no blade (112, 115) is received in the blade supply container (110), and the blade supply container (110) comprising a spring means (114) arranged so that a blade stack (111) received in the blade supply container (110) is impinged upon with spring force, and the empty indicator (113a) is actuated by the spring means (114) when no blade (112, 115) is received in the blade supply container (110), wherein the empty indicator (113a) is arranged on the support block (113);

a blade disposal container (120) including a blade disposal container upper side and a blade disposal container underside, the blade disposal container (120) being embodied to receive blades (120) to be disposed of; and a detachable and reconnectable means for connecting (130, 131, 132) the blade supply container (110) and blade disposal container (120) detachably to one another.

16. The blade dispenser according to claim 15, wherein the detachable and reconnectable means for connecting (130, 131, 132) connects the blade supply container underside and the blade disposal container upper side detachably to one another.

17. The blade dispenser according to claim 15, wherein the detachable and reconnectable means for connecting (130, 131, 132) includes a sliding closure.

18. The blade dispenser according to claim 17, wherein the sliding closure is configured as a dovetail guide.

19. The blade dispenser according to claim 15, wherein the detachable and reconnectable means for connecting (130, 131, 132) includes a snap-in closure.

20. The blade dispenser according to claim 15, wherein the detachable and reconnectable means for connecting (130, 131, 132) comprises, on the blade supply container (110) and on the blade disposal container (120), flanges (131, 132) that can be slid into one another.

21. The blade dispenser according claim 15, the blade supply container (110) further including an access opening (117) through which at least one blade (112, 115) of the blade stack (111) is accessible from outside the blade supply container (110).

22. The blade dispenser according to claim 21, the access opening (117) being embodied as an elongated hole on the blade supply container upper side.

23. The blade dispenser according to claim 15, the blade supply container (110) having a bar (160) on the blade supply container upper side (110), wherein the bar (160) forms an inclined plane (161) on the blade supply container upper side.

24. The blade dispenser (100) according to claim 15, wherein the blade supply container (110) comprises means for alignment (151, 152) embodied to orient the blade supply container (110) on a blade changing apparatus.

25. The blade dispenser (100) according to claim 15, wherein the blade disposal container (120) comprises means for alignment (151, 152) embodied to orient the blade disposal container (120) on a blade changing apparatus.

* * * * *